US006382792B1

(12) United States Patent
Khoury

(10) Patent No.: US 6,382,792 B1
(45) Date of Patent: May 7, 2002

(54) OPTICAL DIAGNOSTIC TOOL

(76) Inventor: Elie Khoury, 587, Décarie, St-Laurent, Québec (CA), H4L 3L1

( * ) Notice: Subject to any disclaimer, the term of this patent is extended or adjusted under 35 U.S.C. 154(b) by 0 days.

(21) Appl. No.: 09/567,535

(22) Filed: May 10, 2000

(30) Foreign Application Priority Data

May 11, 1999 (GB) .......................................... 9910785.6

(51) Int. Cl.[7] ................................................ A61B 3/10
(52) U.S. Cl. ...................................................... 351/205
(58) Field of Search ................................ 351/205, 206, 351/207, 208, 209, 210, 214, 216, 217, 218, 221, 245, 246, 223, 224

(56) References Cited

U.S. PATENT DOCUMENTS

| 5,157,427 A | * 10/1992 | Humphrey | .................. 351/205 |
| 5,784,145 A | * 7/1998 | Ghodse et al. | ............... 351/205 |
| 6,022,109 A | * 2/2000 | Dal Santo | .................... 351/221 |

* cited by examiner

Primary Examiner—George Manuel

(57) ABSTRACT

An optical diagnostic tool for allowing an observer to obtain optical information regarding various characteristics of the eyes of an intended patient. The tool includes an enclosure defining a peripheral wall, a patient end wall and an observer end wall. An optical dividing wall is positioned within the enclosure. The optical dividing wall divides the enclosure into a first and a second optical chamber, allowing for the creation of distinct lighting pattern in the first and second optical chambers. A first and a second patient eye aperture both extend through the patient end wall. The first and second patient eye apertures individually establish visual communication respectively with the first and second optical chambers. An observer visual access structure allows the observer to obtain selective optical access to either one or both of the first and second optical chambers and to either one or both of the corresponding first and second patient eye apertures. A selective light emitting structure mounted within the enclosure allows for the creation of the predetermined distinct lighting patterns in the first and second optical chambers.

19 Claims, 4 Drawing Sheets

OPTICAL DIAGNOSTIC TOOL

FIELD OF THE INVENTION

The present invention relates to the general field of ophthalmology and is particularly concerned with a device for determining pupillary response and other ophtalmologic parameters so as to act as an optical diagnostic tool.

BACKGROUND OF THE INVENTION

The prior art discloses various devices for measuring and recording the size of the pupil of the human eye as well as of laboratory animals. Measurement of the pupil size and reactions is an important indicator of autonomic nervous system activity and the general physiological state of the subject.

The visual pathways and the oculomotor system reflect much of the status of the nervous system as a whole. Approximately 35% of the sensory nervous fibers entering the brain are in the two optic nerves. It is estimated that 65% of intracranial diseases exhibit neuro-ophthalmic symptoms or signs. Routine neurovisual examination allows physicians and scientists to identify abnormalities indicating neurologic disorders. Important examples are brain tumors, multiple sclerosis, cerebrovascular decease and cerebral aneurysms.

The examination of pupils is particularly helpful for assessing the visual pregeniculate pathways and oculomotor system. Typically, the pupils are inspected while the patient or individual is looking at distance to avoid the pupillary constriction that occurs with a near target. Inspection of the pupils in patients with dark brown irides can be facilitated with a tangentially applied light.

The pupils should be round and equal in diameter, although less than 1 mm. of inequality may be a normal variation. Poor pupillary dilation in dim light may indicate dysfunction of the sympathetic nervous system, and poor pupillary constriction to bright light may indicate parasympathetic dysfunction.

During typical testing of the pupillary reactions to light, the patient is asked to look into the distance and a bright light is shined obliquely into each pupil in turn. Both the distant gaze and the oblique lighting help to prevent a near reaction. The individual performing the test notes both the direct reaction which is the pupillary constriction in the same eye, and the so called consensual reaction which is the pupillary constriction in the opposite eye. Both the afferent pathway and the efferent pathway are responsible for this dual reaction.

As is well known, light stimulation for example of the left retina will result in impulsive which travels up the left optic nerve and divides at the chiasm. Some impulses continue up to the left tract; some cross and continue up the right tract. The light impulse arrives at each pretectal nucleus and stimulate the cell which, in turn, send impulses down the third cranial nerve to the iris sphincter causing each pupil to constrict. It is because of the double decussation, the first in the chiasm and the second between the pretectal nuclei and the Edinger-Westphal nuclei, that the direct pupil response in the left eye equals the consensual response in the right eye.

Insofar, the so called swinging-flashlight test does the most valuable clinical test for optic nerve dysfunction currently available. The abnormality detected with this test is the afferent pupillary defect called, also known as the Marcus Gunn pupil.

To perform the so called swinging-flashlight test, one must dim room illumination and prepare a bright light. The patient maintains fixation on an object typically 15' or more away. The bright light is held directly in front of one eye for 3 to 5 seconds moved rapidly across the bridge of the nose to the front of the other eye for 3 to 5 seconds and then shifted back to the first eye.

This procedure is typically repeated several times until the examiner is certain of the responses. The critical observations to be made are the behavior of the pupil when it is first illuminated. A normal response is initial pupillary constriction followed by variable amounts of redilation. An abnormal response is slow dilation without initial constriction. The relative afferent pupillary defect almost always indicates a lesion in the optic nerve on the affected side, although rarely a large retinal lesion may produce this defect.

In other words, during the swinging-flashlight test, the examiner projects the light on the right eye (e.i.), allowing the right pupil to constrict to a minimum size and subsequently escape to an intermediate size. The light is then quickly swung to the left eye, which constricts from an intermediate to a minimum size, subsequently escaping to an intermediate size. At this point the light is swung again to the right eye and a mental note is made of the intermediate (starting) pupil size and briskness of the response to light. These characteristics should be exactly the same in both eyes as the light is alternatively swung to each eye.

The swinging-flashlight test will determine if the amount of light transmitted from one eye is less than that carried via the fellow eye. When the light is swung to the defective eye, immediate dilation of the pupils occurs instead of the normal initial constriction. This characterizes an afferent pupillary defect.

A partial differential diagnosis includes a retinal detachment, occlusion of a central retinal artery or vein, optic neuritis, and optic neuropathy among others entities.

Although the swinging-flashlight test is widely known and used for evaluating neuro-ophthalmologic defects and more particularly the afferent pupillary defect, it suffers from a set of drawbacks. Indeed, the test is challenging to the observer both technically and mentally. During technical performance of the test, the examiner must swing the light quickly between each eye with substantial consistency in order to achieve relatively valuable and constant observations.

This is particularly difficult since the source of light, typically a small flashlight must be swung between the eyes across the nose bridge of the patient.

Also, during movement of the light source between the eyes, the light source must ideally remain substantially symmetrical and oblique relative to the pupils. This is particularly difficult to perform with consistency.

Also, the intensity of the light being shined through the pupils relatively to the room illumination may also vary considerably and affect interpretation of the test results.

Furthermore, one of the main drawbacks associated with the conventional method of performing the afferent pupillary defect test or the so called swinging-flashlight test involves the need for the observer to make a mental note of the intermediate (starting) pupil size and briskness of the response to light.

The problem is further compounded by the fact that such mental notes must be made serially for each eye. Needless to say, even with an experienced observer, the conventional method and devices used for performing the afferent pupillary defect test involves a considerable amount of subjectivity. This can lead to erroneous interpretation with detrimental consequences. Accordingly, there exists a need for an improved method and device for performing the afferent pupillary defect test and perform the evaluation of other ophtalmologic parameters. The human eye also provides numerous other parameters such as pupil form, corneal abnormalities and soforth that can be used by the clinician to evaluate not only the health of the observed eye but also the overall health of a given patient. Most clinicians only use a conventional pocket ophtalmoscope to assess these essential parameters at least in part because of the overall complexity of alternative ophtalmologic tools. This in turn, again leads to relatively frequent misdiagnosis that could be avoided should a simple yet efficient tool be available.

Advantages of the present invention include the fact that the proposed methods and devices allow an individual to assess pupillary reaction including detection of the afferent pupillary defect with reduced external variables and parameters that may potentially lead to an erroneous result and interpretations.

More particularly the present device allows for a better control of the base illumination to which the pupils of an intended patient are subjected. Also, the proposed device facilitates the actual swinging of the light source between each pupil in a more standard manner less subjectable to technical variables such as having to skip over the nose bridge of the intended patient and provide a constant symmetrical or otherwise predetermined illumination angle.

Still further, the proposed device allows an intended observer to obtain simultaneous visualization of both pupils of an intended patient subjected to different lighting conditions. This allows an intended observer to decrease the amount of subjectivity associated with conventional pupillary response tests. It reduces the need for the observer to make mental notes of subjective values such as pupillary size and briskness of reaction.

Also, the proposed device allows an intended user to monitor the pupillary response through a signal visualization aperture and allows for various treatments of the optical information including passage through processing optical devices and recording of the information.

Furthermore, the proposed device facilitates the accurate evaluation of a multitude of other general and ophtalmologic tests applied to the eye of patients such as corneal inspection pupil size determination and the like.

Still further, the proposed device allows for realization of the hereinabove mentioned advantages using a relatively simple structure thus providing a device which can be manufactured using conventional forms of manufacturing. The proposed device thus provides a simple and relatively inexpensive yet efficient solution to the hereinabove mentioned drawbacks associated with the conventional method of determining pupillary response.

SUMMARY OF THE INVENTION

In accordance with one embodiment of the invention there is provided an optical diagnostic tool for allowing an observer to obtain optical information regarding various characteristics of the eyes of an intended patient, the eyes including a pupil section the optical diagnostic tool comprising: an enclosure, the enclosure including a peripheral wall, a patient end wall and an observer end wall; an optical dividing means positioned within the enclosure, the optical dividing means dividing the enclosure into a first and a second optical chamber, the optical dividing means allowing the creation of distinct lighting pattern in the first and second optical chambers; a first and a second patient eye aperture both extending through the patient end wall, the first and second patient eye apertures individually establishing visual communication respectively with the first and second optical chambers; a selective observer optical access means positioned adjacent the observer end wall for allowing the observer to obtain selective optical access to either one or both of the first and second optical chambers and to either one or both of the corresponding first and second patient eye apertures; a selective light emitting means mounted within the enclosure for selectively allowing the creation of the predetermined distinct lighting patterns in the first and second optical chambers. Preferably, the optical dividing means includes a dividing wall extending between the patient end wall and the observer end wall.

Conveniently, the selective observer optical means includes a first and a second observer eye aperture, the first and second observer eye apertures being configured, sized and positioned so as to individually establish visual communication respectively with the first and second optical chambers and the first and second patient eye apertures.

Preferably, the selective observer optical means includes a focussing means for focusing the optical information emanating from both the first and second observer eye apertures towards a common viewing area.

Conveniently, the focussing means includes a focusing structure, the focusing structure defining at least a pair of reflective surfaces, the reflective surfaces being configured, sized and positioned so as to focus the optical information emanating from both the first and second observer eye apertures towards the common viewing area. Preferably, the selective observer optical means further includes an optical treatment component positioned adjacent the first and a second observer eye apertures. Conveniently, the optical treatment component includes a pair of lenses positioned adjacent the first and a second observer eye apertures.

Preferably, the selective light emitting means includes a lighting aperture formed in the dividing wall; a light source mounted within the lighting aperture for directing light rays towards the patient end wall; a blocking structure mounted adjacent the lighting aperture for selectively preventing the passage of light rays through the lighting aperture.

Conveniently, the blocking structure has a generally "V"-shaped cross-sectional configuration defining a pair of blocking panels extending at an angle relatively to each other from a common merging apex, the blocking structure being pivotally mounted within the enclosure so that pivotal movement thereof allows the blocking panels to alternatively block the lighting aperture.

Preferably, the lighting aperture, the blocking structure and the light source are positioned adjacent the observer end wall; the light source is attached to the blocking structure so as to pivot solidarly therewith; the observer end wall is provided with a light source aperture extending therethrough; at least a protruding section of the light source protrudes outwardly from the light source aperture; the protruding section being graspable by the observer; whereby the protruding section is intended to be used by the observer for pivoting both the light source and the obstructing structure.

Conveniently, the light source includes an elongated flashlight extending partially along a bisecting axis defined by the blocking panels. Preferably, the selective light emitting means further includes a light ray redirecting means for selectively redirecting light rays emanating from the light source towards the eyes of the patient at predetermined incident angles relative thereto.

Conveniently, said light ray redirecting means includes a set of reflective panels mounted within the enclosure, the reflective panels being positioned, configured and sized for selectively redirecting light rays emanating from the light source towards the eyes of the patient at predetermined incident angles relative thereto.

Preferably, the tool further comprises a scale projecting means for projecting the image of a scale towards the selective observer optical means so as to superpose the image of a scale to the image of the pupil section of the eyes of the patient; whereby the projection of the image of a scale facilitates accurate assessment of the size of the pupil region.

Conveniently, the scale projecting means includes a scale projector for projecting the image of a scale towards the selective observer optical means; an image blocking means for preventing light rays emanating from the image projector from being directed towards the first and a second patient eye aperture.

Preferably, the scale projector includes a scale light source mounted within the enclosure and a scale panel made out of a generally transparent material, the scale panel having scale indices marked thereon, the scale light source and the scale panel being positioned so that light rays emanating from the scale light source project the image of a scale towards the selective observer optical means; the image blocking means including at least one scale reflective panel for preventing light rays emanating from the image projector from being directed towards the first and a second patient eye aperture.

In accordance with the present invention, there is also provided an optical diagnostic tool for allowing an observer to obtain optical information regarding various characteristics of the eyes of an intended patient, the eyes including a pupil sectionthe optical diagnostic tool comprising: an enclosure, the enclosure including a peripheral wall, a patient end wall and an observer end wall; an optical dividing means positioned within the enclosure, the optical dividing means dividing the enclosure into a first and a second optical chamber, the optical dividing means allowing the creation of distinct lighting pattern in the first and second optical chambers, the optical dividing means including a dividing wall extending between the patient end wall and the observer end wall; a first and a second patient eye aperture both extending through the patient end wall, the first and second patient eye apertures individually establishing visual communication respectively with the first and second optical chambers; a selective observer optical access means positioned adjacent the observer end wall for allowing the observer to obtain selective optical access to either one or both of the first and second optical chambers and to either one or both of the corresponding first and second patient eye apertures; a selective light emitting means mounted within the enclosure for selectively allowing the creation of a predetermined distinct pattern intensity in the first and second optical chambers; the selective light emitting means including a lighting aperture formed in the dividing wall, a light source mounted within the lighting aperture for directing light rays towards the patient end wall and a blocking structure mounted adjacent the lighting aperture for selectively preventing the passage of light rays through the lighting aperture.

Preferably, the selective light emitting means further includes a light ray redirecting means for selectively redirecting light rays emanating from the light source towards the eyes of the patient at predetermined incident angles relative thereto.

BRIEF DESCRIPTION OF THE DRAWINGS

An embodiment of the present invention will now be disclosed, by way of example, in reference to the following drawings in which.

DETAILED DESCRIPTION OF THE DRAWINGS

Figure 1:
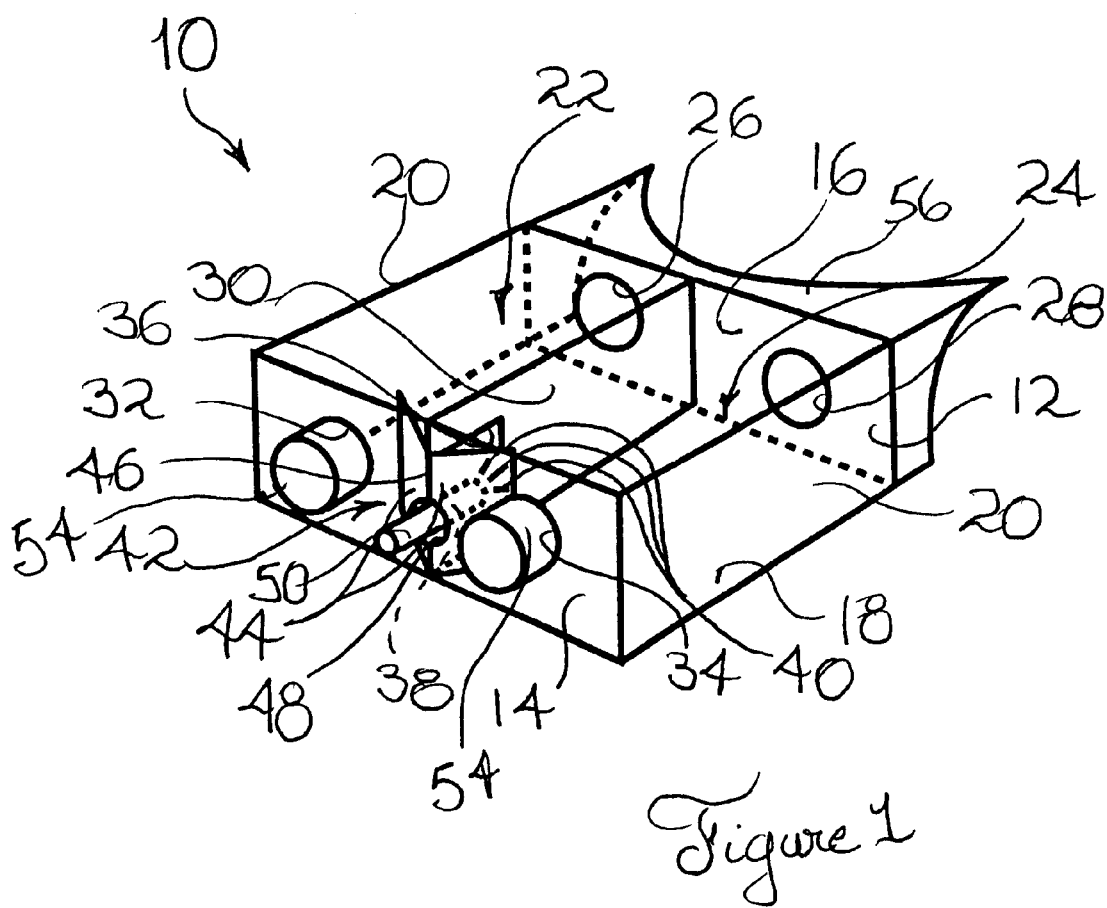
FIG. 1: in a schematic perspective view, illustrates an optical diagnostic tool in accordance with an embodiment of the present invention.

Referring to FIG. 1, there is shown in a schematic perspective view with sections taken out, an optical diagnostic tool 10 for determining various ophtalmologic parameters such as pupillary response in accordance with an embodiment of the present invention.

The device 10 includes an enclosure formed by a peripheral wall, a patient end wall 12 and an observer end wall 14. Although the peripheral wall may take any suitable shape, FIGS. 1 through 5, illustrate a peripheral wall defining a top wall 16, a bottom wall 18 and a pair of opposed side walls 20.

The tool 10 also includes an optical dividing means positioned within said enclosure. The optical dividing means divides the enclosure to a first optical chamber 22 and a second optical chamber 24. The optical dividing means is configured so as to allow the creation of distinct lighting patterns in the first and second optical chambers.

A first and a second patient eye aperture 26, 28 extend through the patient end wall 12. The first and second patient eye apertures 26, 28 individually establish visual communication respectively with the first and second optical chambers 22, 24.

A selective observer optical access means positioned adjacent the observer end wall 14 is provided for allowing the intended observer to obtain selective optical access to either one or both of the first and second optical chambers 22, 24 and to either one or both of the corresponding first and second patient eye apertures 26, 28. Also, a selective light emitting means mounted within the enclosure is provided for selectively allowing the creation of a predetermined distinct lighting pattern in the first and second optical chambers 22, 24. Preferably, although by no means exclusively, the optical dividing means includes a dividing wall 30 extending between the patient end wall 16 and the observer end wall 14.

The selective observer optical means preferably includes a first and a second observer eye aperture 32, 34. The first and second observer eye apertures 32, 34 are configured, sized and positioned so as to individually establish visual communication respectively with the first and second optical chambers 22, 24 and the first and second patient eye apertures 26, 28.

The selective light emitting means preferably includes a lighting aperture 36 formed in the dividing wall 30. The selective light emitting means also include a light source 38 mounted within the lighting aperture 36 for directing light rays 40 towards the patient end wall 16. The selective light emitting means further includes a blocking structure 42 mounted adjacent the lighting aperture 36 for selectively preventing the passage of the light rays 40 through the lighting aperture 36.

Figures 3, 4:
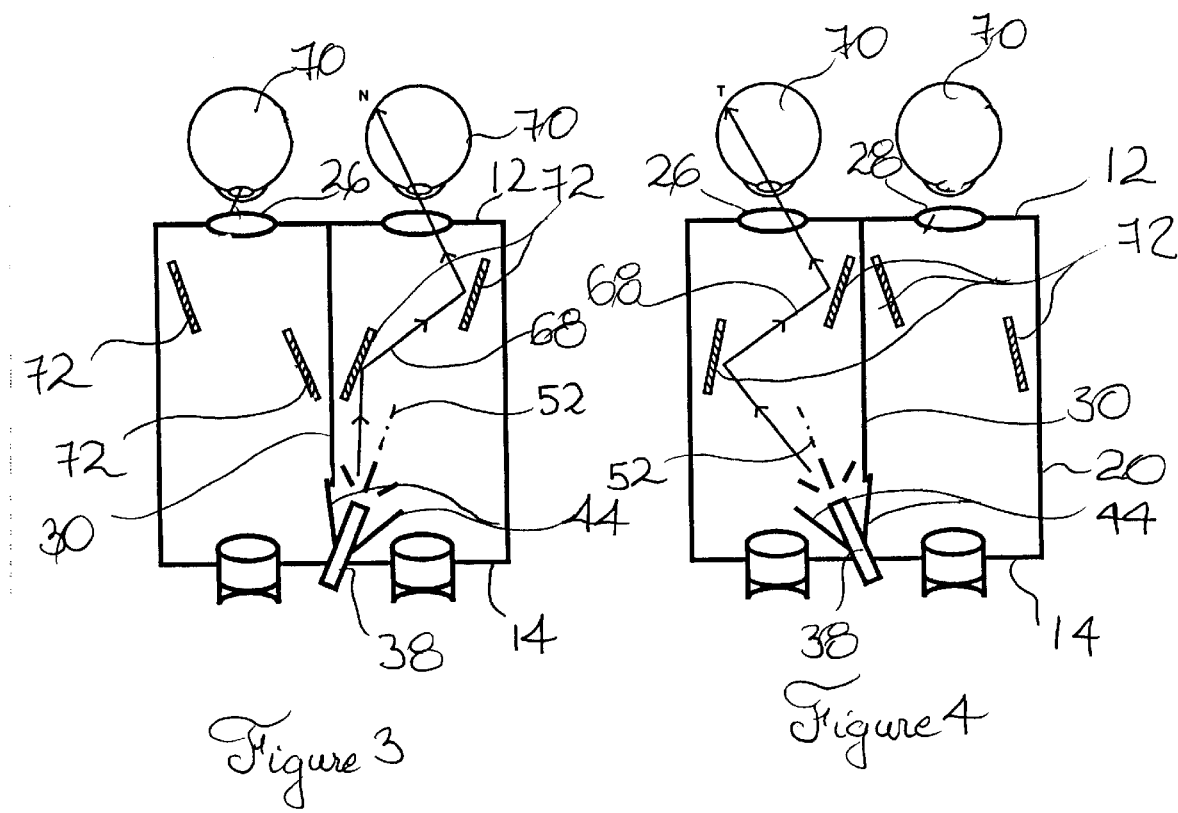
FIG. 3: in a longitudinal cross sectional view, illustrates the device shown in FIGS. 1 and 2 at its light emitting means directed towards the left eye of an intended patient, the device being shown with optional light ray redirecting means.
FIG. 4: in a longitudinal cross sectional view, illustrates the device shown in FIGS. 1 and 2 at its light emitting means directed toward the right eye of an intended patient, the device being shown with optional light ray redirecting means.

The blocking structure 42 preferably has a generally "V" shaped cross sectional configuration defining a pair of blocking panels 44 extending at an angle relatively to each other from a common merging apex 46. The blocking structure is pivotally mounted within the enclosure so that pivotal movement thereof allows the blocking panels 44 to alternatively block the lighting aperture 36 as shown in FIGS. 3 and 4.

A light source 38 is preferably pivotally mounted so as to pivot solidarity with the blocking structure 42. Preferably, although by no means exclusively, the blocking structure 42 and the light source 38 are positioned adjacent the observer end wall 14. Also, the observer end wall 14 is preferably provided with a light source aperture 48 coming therethrough. When a light source aperture 48 is provided, at least a protruding section 50 of the light source 38 protrudes outwardly from the light source aperture 48 so as to be graspable by an intended observer. The protruding section 50 is thus intended to be used by the observer for pivoting both the light source 38 and the obstructing structure 42 attached thereto. Preferably, although by no means exclusively, the light source includes an elongated miniature flashlight extending partially along a bisecting axis 52 defined by the blocking panels 44.

An abutment cylinder 54 preferably extends outwardly from the outer peripheral edge of both the first and second observer eye apertures 32, 34. Optionally, a head abutment structure (not shown) could also be positioned adjacent the first and second observer eye apertures 32, 34 for allowing the abutting stabilization of the observer's head against the tool 10. Similarly, a patient head abutment structure 56 preferably extends outwardly from the outer surface of the patient end wall 12. Patient abutment structure 56 is preferably made out of a cushioned relatively resilient material. The configuration of the patient head abutment structure 56 is preferably specifically designed for allowing the head of the intended patient to comfortably rest on the tool 10 so as to improve the comfort of the intended patient and reduce the risk of inadvertent head movement by the latter. It should be understood that the external configuration of the patient head abutment component 56 preferably conforms to the contour of the frontal surface of the head of an intended patient but could vary from that shown in FIGS. 1 through 5 without departing from the scope of the present invention.

Figure 2:
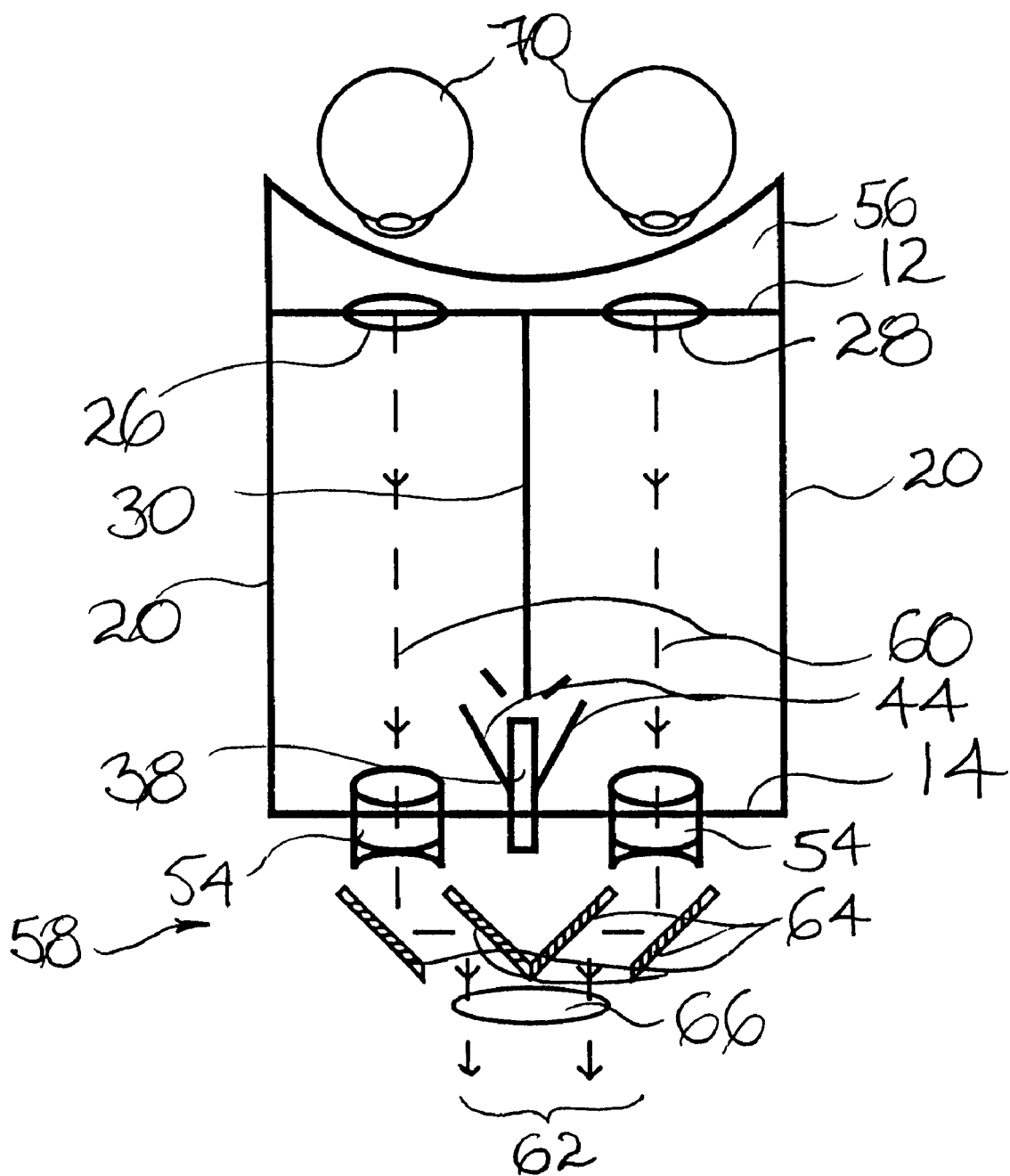
FIG. 2: in a longitudinal cross sectional view with section taken out, illustrates an optical diagnostic tool shown in FIG. 1 with optional light ray focusing means positioned substantially centrally.
Figure 5:
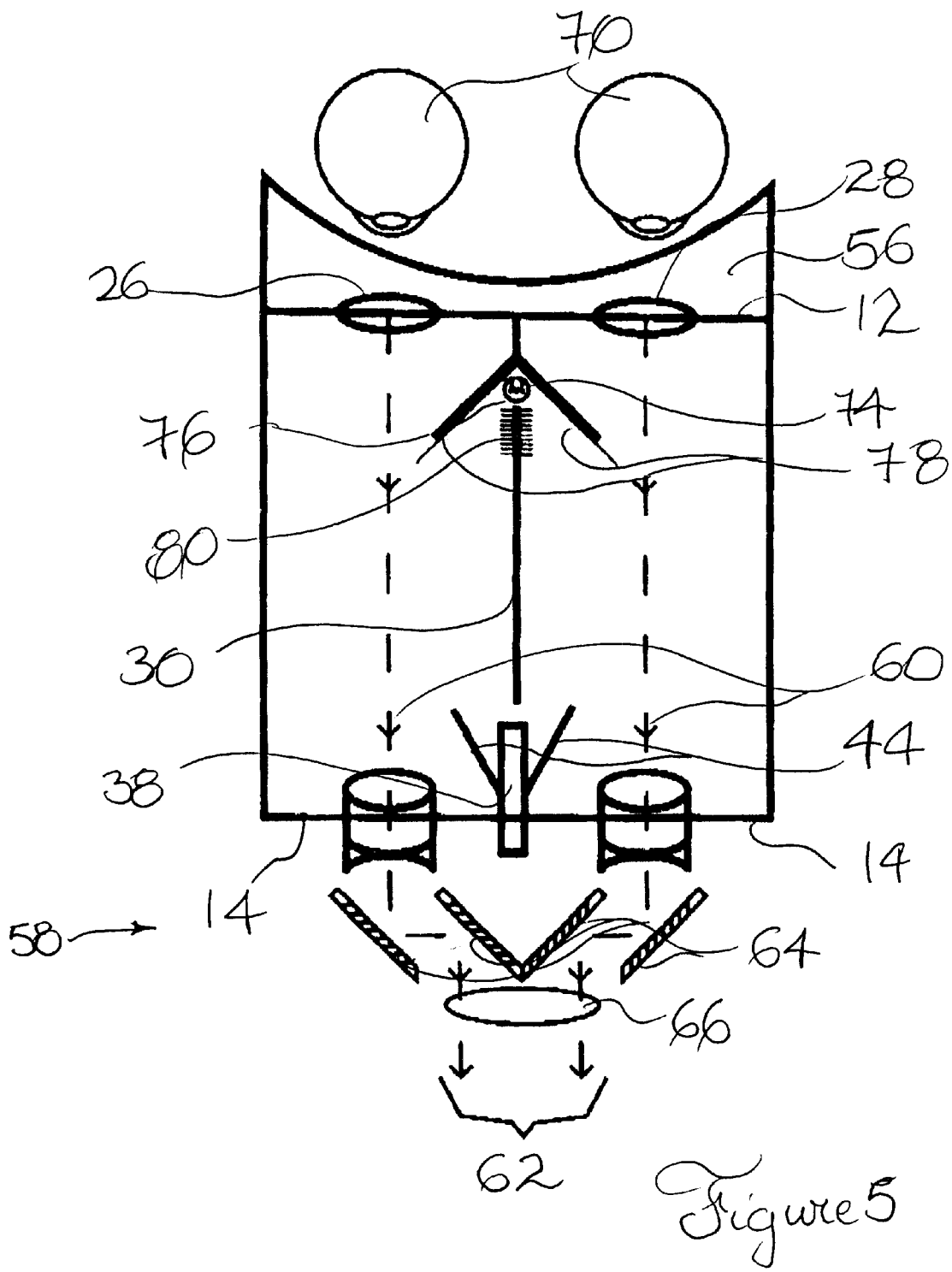
FIG. 5: in a longitudinal cross sectional view, illustrates the device shown in FIG. 2 having an optional scale projecting means.

Referring now more specifically to FIGS. 2 and 5, there is shown an embodiment of the invention further including a focusing means 58 for focusing the optical information schematically designated by the arrows LX emanating from both the first and second observer eye apertures 26, 28 with a common viewing area 62. Preferably, the focusing means includes a focusing structure defining at least a pair of reflecting surfaces 64. The focusing reflecting surfaces 64 are configured, sized and positioned so as to focus the optical information 60 emanating from both the first and second observer eye apertures 26, 28 towards the common viewing area 62. Furthermore, optionally, with or without the focusing means 58, the tool 10 may optionally be further provided with optical treatment components positioned adjacent the first and second observer eye apertures 32, 34. The optical treatment component schematically illustrated by the component 66 may take the form of lenses, reticles or any other suitable optical treatment component. The optical treatment component could be provided anywhere along the optical path including within the viewing abutment cylinders 54. Still further, optionally, the tool 10 may be provided with a recording medium such as a video camera, a photograph camera or any other suitable means for recording the visual information 60 emanating from the first and second patient eye apertures 26, 28.

Referring now more specifically to FIGS. 3 and 4, there is shown a tool 10 further including an optional light ray redirecting means for selectively redirecting light rays schematically designated by the reference numeral 68 towards the eyes 70 of an intended patient at predetermined incident angles relative thereto. The light ray redirecting means typically includes a set of redirecting reflective panels 72 that are configured, sized and positioned for selectively redirecting the light rays 68 emanating from the light source 74. The reflective surfaces 72 allow the light rays 68 to be selectively directed toward the retina portion of the eyes 70 at various preferably symmetrical angles thus allowing testing of the pupillary reflexes and other parameters attendant on the specific retinal location being examined. In other words, the present invention further allows for detection of discreet pupillary reflex differences created by the discreet localized defects of the retina of the intended patient. Preferably, the reflective surfaces 62 are provided with angle adjustment means (not shown) allowing selective variation of their respective angles during the examination procedure through a set of simple ergonomic steps performed by the observer.

Referring now more specifically to FIG. 5, there is shown an embodiment of the invention further including an optional scale projecting means for projecting the image of a scale towards the selective observer optical means so as to superpose the image of the scale to the image of the pupil section of the eyes 70 of the patient. The projection of the image of the scale facilitates accurate assessment of the size of the pupillary region of the eye. The scale projecting means typically includes a scale projector having a scale light source 74 positioned within a scale light source aperture 76 formed in the dividing wall 30. An image blocking means for preventing light rays emanating from the image projector being directed towards the first and second patient eye apertures 26, 28 is further provided. The image blocking means typically includes at least one and preferably two scale reflective panels 78 symmetrically and centrally disposed. The scale light source aperture 76 is adapted to project light rays through a scale panel schematically indicated by the reference numeral 80 preferably made out of a generally transparent material and having scale indices marked thereon. The light emanating from the scale light source projects the scale marked on the scale panel 80 towards the selective observer optical means superposing the scale image over the viewed image of the pupils of the intended user and thus allowing for accurate measurement of the size thereof.

In use, the intended patient is invited to focus his/her view on a rear or virtual target that can be easily adjusted so as to compensate for accommodation. The intended observer merely needs to use the various components associated with the tool 10 to perform an accurate evaluation of various parameters of the eyes 70 of the intended patient.

The embodiments of the invention in which an exclusive priviledge or property is claimed are defined as follows:

1. An optical diagnostic tool for allowing an observer to obtain optical information regarding various characteristics of the eyes of an intended patient, said eyes including a pupil sectionsaid optical diagnostic tool comprising:
- an enclosure, said enclosure including a peripheral wall, a patient end wall and an observer end wall;
- an optical dividing means positioned within said enclosure, said optical dividing means dividing said enclosure into a first and a second optical chamber, said optical dividing means allowing the creation of distinct lighting pattern in said first and second optical chambers;
- a first and a second patient eye aperture both extending through said patient end wall, said first and second patient eye apertures individually establishing visual communication respectively with said first and second optical chambers;
- a selective observer optical access means positioned adjacent said observer end wall for allowing said observer to obtain selective optical access to either one or both of said first and second optical chambers and to either one or both of said corresponding first and second patient eye apertures;
- a selective light emitting means mounted within said enclosure for selectively allowing the creation of said predetermined distinct lighting patterns in said first and second optical chambers.

2. An optical diagnostic tool as recited in claim 1 wherein said optical dividing means includes a dividing wall extending between said patient end wall and said observer end wall.

3. An optical diagnostic tool as recited in claim 2 wherein said selective light emitting means includes
- a lighting aperture formed in said dividing wall;
- a light source mounted within said lighting aperture for directing light rays towards said patient end wall;
- a blocking structure mounted adjacent said lighting aperture for selectively preventing the passage of light rays through said lighting aperture.

4. An optical diagnostic tool as recited in claim 3 wherein said blocking structure has a generally "V"-shaped cross-sectional configuration defining a pair of blocking panels extending at an angle relatively to each other from a common merging apex, said blocking structure being pivotally mounted within said enclosure so that pivotal movement thereof allows said blocking panels to alternatively block said lighting aperture.

5. An optical diagnostic tool as recited in claim 4 wherein said light source is pivotally mounted so as to pivot solidarly with said blocking structure.

6. An optical diagnostic tool as recited in claim 5 wherein
- said lighting aperture, said blocking structure and said light source are positioned adjacent said observer end wall;
- said light source is attached to said blocking structure so as to pivot solidarly therewith;
- said observer end wall is provided with a light source aperture extending therethrough;
- at least a protruding section of said light source protrudes outwardly from said light source aperture;
- said protruding section being graspable by said observer; whereby said protruding section is intended to be used by said observer for pivoting both said light source and said obstructing structure.

7. An optical diagnostic tool as recited in claim 5 wherein said light source includes an elongated flashlight extending partially along a bisecting axis defined by said blocking panels.

8. An optical diagnostic tool as recited in claim 3 wherein said selective light emitting means further includes a light ray redirecting means for selectively redirecting light rays emanating from said light source towards said eyes of said patient at predetermined incident angles relative thereto.

9. An optical diagnostic tool as recited in claim 8 wherein said light ray redirecting means includes a set of reflective panels mounted within said enclosure, said reflective panels being positioned, configured and sized for selectively redirecting light rays emanating from said light source towards said eyes of said patient at predetermined incident angles relative thereto.

10. An optical diagnostic tool as recited in claim 1 wherein said selective observer optical means includes a first and a second observer eye aperture, said first and second observer eye apertures being configured, sized and positioned so as to individually establish visual communication respectively with said first and second optical chambers and said first and second patient eye apertures.

11. An optical diagnostic tool as recited in claim 10 wherein said selective observer optical means includes a focussing means for focusing the optical information emanating from both said first and second observer eye apertures towards a common viewing area.

12. An optical diagnostic tool as recited in claim 11 wherein said focussing means includes a focusing structure, said focusing structure defining at least a pair of reflective surfaces, said reflective surfaces being configured, sized and positioned so as to focus the optical information emanating from both said first and second observer eye apertures towards said common viewing area.

13. An optical diagnostic tool as recited in claim 10 wherein said selective observer optical means further includes an optical treatment component positioned adjacent said first and a second observer eye apertures.

14. An optical diagnostic tool as recited in claim 13 wherein said optical treatment component includes a pair of lenses positioned adjacent said first and a second observer eye apertures.

15. An optical diagnostic as recited in claim 1 further comprising a scale projecting means for projecting the image of a scale towards said selective observer optical means so as to superpose said image of a scale to the image of said pupil section of said eyes of said patient; whereby the projection of the image of a scale facilitates accurate assessment of the size of said pupil region.

16. An optical diagnostic as recited in claim 15 wherein said scale projecting means includes
- a scale projector for projecting said image of a scale towards said for projecting the image of a scale said selective observer optical means;
- an image blocking means for preventing light rays emanating from said image projector from being directed towards said first and a second patient eye aperture.

17. An optical diagnostic as recited in claim 16 wherein
- said scale projector includes a scale light source mounted within said enclosure and a scale panel made out of a generally transparent material, said scale panel having scale indices marked thereon, said scale light source and said scale panel being positioned so that light rays emanating from said scale light source project said image of a scale towards said selective observer optical means;
- said image blocking means including at least one scale reflective panel for preventing light rays emanating from said image projector from being directed towards said first and a second patient eye aperture.

18. An optical diagnostic tool for allowing an observer to obtain optical information regarding various characteristics of the eyes of an intended patient, said eyes including a pupil section said optical diagnostic tool comprising:

an enclosure, said enclosure including a peripheral wall, a patient end wall and an observer end wall;

an optical dividing means positioned within said enclosure, said optical dividing means dividing said enclosure into a first and a second optical chamber, said optical dividing means allowing the creation of distinct lighting pattern in said first and second optical chambers, said optical dividing means including a dividing wall extending between said patient end wall and said observer end wall;

a first and a second patient eye aperture both extending through said patient end wall, said first and second patient eye apertures individually establishing visual communication respectively with said first and second optical chambers;

a selective observer optical access means positioned adjacent said observer end wall for allowing said observer to obtain selective optical access to either one or both of said first and second optical chambers and to either one or both of said corresponding first and second patient eye apertures;

a selective light emitting means mounted within said enclosure for selectively allowing the creation of a predetermined distinct pattern intensity in said first and second optical chambers; said selective light emitting means including a lighting aperture formed in said dividing wall, a light source mounted within said lighting aperture for directing light rays towards said patient end wall and a blocking structure mounted adjacent said lighting aperture for selectively preventing the passage of light rays through said lighting aperture.

19. An optical diagnostic tool as recited in claim 18 wherein said selective light emitting means further includes a light ray redirecting means for selectively redirecting light rays emanating from said light source towards said eyes of said patient at predetermined incident angles relative thereto.

* * * * *